United States Patent
Khayrallah et al.

(10) Patent No.: US 9,649,291 B2
(45) Date of Patent: May 16, 2017

(54) TREATMENT FOR OBESITY

(71) Applicants: Jazz Pharmaceuticals International III Limited, Hamilton (BM); SK Biopharmaceuticals Co., Ltd., Seoul (KR)

(72) Inventors: Moise A. Khayrallah, Morrisville, NC (US); Gary Bream, Cary, NC (US); Stephen E. Butts, Holly Springs, NC (US)

(73) Assignees: Jazz Pharmaceuticals International III Limited, Hamilton (BM); SK Biopharmaceuticals Co., Ltd., Seoul (KR)

( * ) Notice: Subject to any disclaimer, the term of this patent is extended or adjusted under 35 U.S.C. 154(b) by 0 days.

(21) Appl. No.: 14/955,646

(22) Filed: Dec. 1, 2015

(65) Prior Publication Data

US 2016/0081970 A1    Mar. 24, 2016

Related U.S. Application Data

(63) Continuation of application No. 14/334,694, filed on Jul. 18, 2014, now Pat. No. 9,226,910.

(60) Provisional application No. 61/847,593, filed on Jul. 18, 2013.

(51) Int. Cl.
  *A61K 31/27*    (2006.01)
  *A61K 9/00*    (2006.01)
  *A61K 9/48*    (2006.01)

(52) U.S. Cl.
  CPC ............ *A61K 31/27* (2013.01); *A61K 9/0053* (2013.01); *A61K 9/48* (2013.01)

(58) Field of Classification Search
  CPC .................................................. A61K 31/27
  See application file for complete search history.

(56) References Cited

U.S. PATENT DOCUMENTS

| | | | |
|---|---|---|---|
| 5,705,640 A | 1/1998 | Choi et al. | |
| 5,756,817 A | 5/1998 | Choi et al. | |
| 5,955,499 A | 9/1999 | Choi et al. | |
| 6,140,532 A | 10/2000 | Choi et al. | |
| 8,232,315 B2 | 7/2012 | Lee et al. | |
| 8,440,715 B2 | 5/2013 | Ahnaou et al. | |
| 8,552,060 B2 | 10/2013 | Palumbo et al. | |
| 8,623,913 B2 | 1/2014 | Melnick et al. | |
| 8,729,120 B2 | 5/2014 | Sporn | |
| 8,741,950 B2 | 6/2014 | Khayrallah et al. | |
| 9,226,910 B2 * | 1/2016 | Khayrallah ............ A61K 31/27 | |
| 2005/0080268 A1 | 4/2005 | Choi et al. | |
| 2008/0039529 A1 | 2/2008 | Sporn | |
| 2008/0090902 A1 | 4/2008 | Pandey et al. | |
| 2012/0004300 A1 | 1/2012 | Lee et al. | |
| 2012/0245226 A1 | 9/2012 | Lee et al. | |
| 2012/0252892 A1 | 10/2012 | Lee et al. | |
| 2013/0137764 A1 | 5/2013 | Ahnaou et al. | |
| 2014/0243406 A1 | 8/2014 | Khayrallah et al. | |
| 2014/0275244 A1 | 9/2014 | Khayrallah et al. | |

FOREIGN PATENT DOCUMENTS

| | | |
|---|---|---|
| EP | 0633023 A2 | 1/1995 |
| EP | 2543660 A1 | 1/2013 |
| WO | WO 96/07637 A1 | 3/1996 |
| WO | WO 96/24577 A1 | 8/1996 |
| WO | WO 96/32375 A1 | 10/1996 |
| WO | WO 98/15526 A1 | 4/1998 |
| WO | WO 98/17636 A1 | 4/1998 |
| WO | WO 2006/050037 A1 | 5/2006 |
| WO | WO 2006/133393 A1 | 12/2006 |
| WO | WO 2007/018496 A1 | 2/2007 |
| WO | WO 2008/048801 A2 | 4/2008 |
| WO | WO 2009/129181 A1 | 10/2009 |
| WO | WO 2011/005473 A2 | 1/2011 |

OTHER PUBLICATIONS

Amsterdam et al. "A single-site, double-blind, placebo-controlled, dose-ranging study of YKP10A—a putative, new antidepressant", *Progress in Neuro-Psychopharmacol. Biol. Psychiatry* 26:1333-1338 (2002).

Gordon et al. "Abstracts of the 28th Annual Meeting", *Soc. NeuroSci.* 24:1490-1491 (1998).

Hasan et al., "How to Keep the Brain Awake? The Complex Molecular Pharmacogenetics of Wake Promotion," *Neuropsychopharmacology* 34:1625-1640 (2009).

Notification of Transmittal of the International Search Report and the Written Opinion of the International Searching Authority, or the Declaration corresponding International Application No. PCT/2014/047186 mailed Dec. 4, 2014.

Notification Concerning Transmittal of International Preliminary on Patentability corresponding International Application No. PCT/2014/047186 mailed Jan. 28, 2016.

Extended European Search Report corresponding European Application No. 14825724.9 dated Dec. 15, 2016.

* cited by examiner

*Primary Examiner* — Paul V Ward
(74) *Attorney, Agent, or Firm* — Myers Bigel, P.A.

(57) ABSTRACT

The present invention relates to a method for treating or preventing obesity in a subject in need thereof, comprising administering to the subject a therapeutically effective amount of certain carbamate compounds. The invention further relates to methods for reducing body weight and/or reducing food intake in a subject in need thereof, comprising administering to the subject a therapeutically effective amount of certain carbamate compounds.

20 Claims, No Drawings

TREATMENT FOR OBESITY

STATEMENT OF PRIORITY

This application is a continuation of U.S. patent application Ser. No. 14/334,694, filed Jul. 18, 2014 which claims the benefit of U.S. Provisional Application Ser. No. 61/847,593, filed Jul. 18, 2013, the entire contents of each of which are incorporated by reference herein.

FIELD OF THE INVENTION

The present invention relates to a method for treating or preventing obesity in a subject in need thereof, comprising administering to the subject a therapeutically effective amount of certain carbamate compounds. The invention further relates to methods for reducing body weight and/or reducing food intake in a subject in need thereof, comprising administering to the subject a therapeutically effective amount of certain carbamate compounds.

BACKGROUND

Obesity is worldwide health problem that is reaching epidemic proportions. As of 2008 the World Health Organization estimates that at least 500 million adults are obese. The United States has the highest rates of obesity in the developed world. It was reported in 2010 that 35.7% of US adults are obese. Overweight and obesity are the fifth leading risk for global deaths.

Obesity is a complex disease influenced by genetics, diet, exercise, and a complex biology. Bariatric surgery to reduce the size of the stomach (gastric bypass surgery) is the only effective treatment for causing weight loss in morbidly obese people. Drugs to treat obesity can be divided into three groups: those that reduce food intake or appetite suppressants; those that alter metabolism or block the absorption of fat; and those that increase thermogenesis. Currently, there are only two drugs approved by the FDA for the long-term treatment of obesity: the fat absorption blocker orlistat (XENICAL®, ALLI®) and the appetite suppressant sibutramine (MERIDIA®). These drugs cause serious side effects and only result in modest weight loss. Thus, discovery of novel obesity treatments is urgently needed.

SUMMARY OF EMBODIMENTS OF THE INVENTION

The present invention provides an effective and convenient method for treatment or prevention of obesity and to help people reduce body weight and/or food intake. Thus, in one aspect the present invention is directed to a method for treating obesity in a subject in need thereof, comprising administering to the subject a therapeutically effective amount of a compound of Formula I:

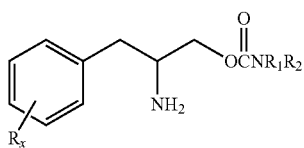

(I)

or a pharmaceutically acceptable salt or ester thereof; wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms; x is an integer of 0 to 3, with the proviso that R may be the same or different when x is 2 or 3; $R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom; wherein the subject reduces body weight, thereby treating the obesity.

In another aspect the present invention is directed to a method for reducing body weight in a subject in need thereof, comprising administering to the subject a therapeutically effective amount of a compound of Formula I:

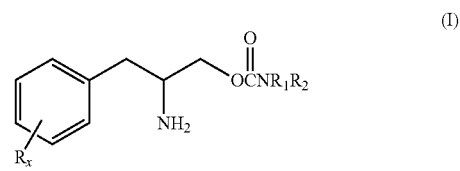

(I)

or a pharmaceutically acceptable salt or ester thereof; wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms; x is an integer of 0 to 3, with the proviso that R may be the same or different when x is 2 or 3; $R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom; wherein the subject reduces body weight.

In another aspect the present invention is directed to a method for reducing food intake in a subject in need thereof, comprising administering to the subject a therapeutically effective amount of a compound of Formula I:

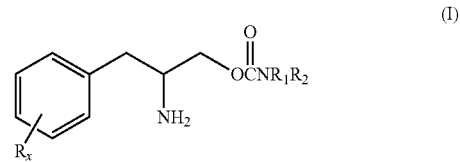

(I)

or a pharmaceutically acceptable salt or ester thereof; wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms; x is an integer of 0 to 3, with the proviso that R may be the same or different when x is 2 or 3; $R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom; wherein the subject reducing food intake.

In some embodiments of the invention the methods comprise the step of administering to the subject an effective amount of an enantiomer of Formula I substantially free of other enantiomers or an enantiomeric mixture wherein one enantiomer of Formula I predominates.

In some embodiments, the compound of Formula I is a compound of Formula Ia:

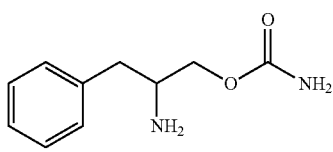

(Ia)

or a pharmaceutically acceptable salt or ester thereof.

In some embodiments, the compound of Formula I is a compound of Formula Ib:

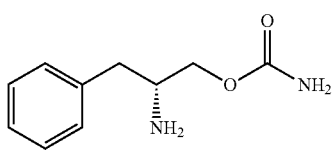

(Ib)

or a pharmaceutically acceptable salt or ester thereof. This compound is named (R)-(beta-amino-benzenepropyl)carbamate or O-carbamoyl-(D)-phenylalaninol and has alternatively been called ADX-N05, SKL-N05, SK-N05, YKP10A, and R228060.

Embodiments of the invention include use of a compound of Formula I for treating obesity in a subject in need thereof. Other embodiments of the invention include use of a compound of Formula I for reducing body weight and/or food intake in a subject in need thereof.

Embodiments of the invention include the use, for the preparation of a medicament for the treatment of obesity, of a compound of Formula I. Other embodiments of the invention include use, for reducing body weight and/or food intake in a subject in need thereof, of a compound of Formula I.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

DEFINITIONS

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±20%, ±10%, ±5%, ±1%, ±0.5%, or even ±0.1% of the specified amount.

The terms "comprise," "comprises," and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" when used in a claim or the description of this invention is not intended to be interpreted to be equivalent to "comprising."

As used herein, the terms "increase," "increases," "increased," "increasing," and similar terms indicate an elevation of at least about 25%, 50%, 75%, 100%, 150%, 200%, 300%, 400%, 500% or more.

As used herein, the terms "reduce," "reduces," "reduced," "reduction," and similar terms mean a decrease of at least about 5%, 10%, 15%, 20%, 25%, 35%, 50%, 75%, 80%, 85%, 90%, 95%, 97% or more. In particular embodiments, the reduction results in no or essentially no (i.e., an insignificant amount, e.g., less than about 10% or even 5%) detectable activity or amount.

"Effective amount" as used herein refers to an amount of a compound, composition and/or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of skill in the art by reference to the pertinent texts and literature and/or by using routine experimentation.

By the term "treat," "treating," or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. With respect to obesity, the term refers to, e.g., a decrease in body mass index, a decrease in body weight, and/or a decrease in body fat. In some embodiments, treatment provides a reduction in body weigh by at least about 5%, e.g., about 10%, 15%, or 20%.

A "therapeutically effective" amount as used herein is an amount that is sufficient to treat (as defined herein) the subject. Those skilled in the art will appreciate that the therapeutic effects need not be complete or curative, as long as some benefit is provided to the subject.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention. With respect to obesity, the term refers to, e.g., preventing obesity from occurring if the treatment is administered prior to the onset of the obese condition. In some embodiments, prevention refers to a decrease in the amount of body weight gained compared to the amount of body weight gained in the absence of administration of the compounds of the invention.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "subject" of the invention includes any animal that has or is susceptible to obesity or is in need of reducing body weight, body weight gain, and/or food intake. Such a subject is generally a mammalian subject (e.g., a laboratory animal such as a rat, mouse, guinea pig, rabbit, primate, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects include males and/or females of any age, including neonates, juveniles, adolescents, adults and geriatric subjects.

A "subject in need" of the methods of the invention can be a subject known to have, suspected of having, or having an increased risk of developing overweight or obesity.

As used herein the term "body mass index" or "BMI" means the ratio of weight in Kg divided by the height in meters, squared.

As used herein the term "overweight" refers to a BMI between 25 and 30 in adult humans. For people under 20 "overweight" is defined as a BMI between the 85th and 95th percentile compared to people of the same age.

As used herein the term "obesity" refers to a BMI between 30 and 40 in adult humans. For people under 20 "obesity" is defined as a BMI above the 95th percentile compared to people of the same age. As used herein, the term can include both obesity and morbid obesity.

As used herein the term "morbid obesity" refers to a BMI greater than 40 in adult humans.

As used herein the term "body weight" refers to the weight of a subject's body.

As used herein the term "body weight gain" refers to the increase in weight of a subject's body over time.

As used herein the term "food intake" refers to the intake of calories in any form, including without limitation food, drink, intravenous, or enteral.

The term "pharmaceutically acceptable salts or esters" shall mean non-toxic salts or esters of the compounds employed in this invention which are generally prepared by reacting the free acid with a suitable organic or inorganic base or the free base with a suitable organic or inorganic acid. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, sodium, stearate, subacetate, succinate, tannate, tartrate, teoclate, tosylate, triethiodide, and valerate.

As used herein the term "concomitant administration" or "combination administration" of a compound, therapeutic agent or known drug with a compound of the present invention means administration of a known medication or drug and, in addition, the one or more compounds of the invention at such time that both the known drug and the compound will have a therapeutic effect. In some cases this therapeutic effect will be synergistic. Such concomitant administration can involve concurrent (i.e., at the same time), prior, or subsequent administration of the known drug with respect to the administration of a compound of the present invention. A person of skill in the art, would have no difficulty determining the appropriate timing, sequence and dosages of administration for particular drugs and compounds of the present invention.

In addition, in some embodiments, the compounds of this invention will be used, either alone or in combination with each other or in combination with one or more other therapeutic medications as described above, or their salts or esters, for manufacturing a medicament for the purpose of providing treatment for obesity to a patient or subject in need thereof.

The present invention is based in part on the discovery that phenylalkylamino carbamates of Formula I have novel and unique pharmacological properties. Without being limited by mechanism, it is thought that the compounds of Formula I function in part by increasing dopamine levels. The neurotransmitter dopamine mediates the reward value of food and it has been found that obese individuals have decreased dopamine receptor D2 availability. Dopamine modulates motivation and reward circuits and hence dopamine deficiency in obese individuals may perpetuate pathological eating as a means to compensate for decreased activation of these circuits. Thus, strategies aimed at improving dopamine function may be beneficial in the treatment of obesity. Amphetamines and amphetamine-like drugs suppress appetite due to stimulation of dopamine signaling and have been used for decades as appetite suppressants to treat obesity; however their appetite suppressant effects are linked to a high risk of addiction. In nonclinical studies in mice, rats, and dogs, administration of the compound of Formula Ib is associated with decreases in body weight and/or body weight gain as well as reductions in food consumption. The present compounds, however, show no clear abuse potential; the compound of Formula Ib was not reinforcing in the classic rat self-administration model and showed no significant rewarding properties in the place preference model. In a 6-week clinical study in major depressive disorder patients examining the antidepressant effects of the compound of Formula Ib, the compound was associated with a dose-related decrease in weight relative to placebo treated patients. There was also an increase in reporting of anorexia in the compound-treated groups. For these reasons the compounds of Formula I are especially suitable for reduction in body weight and treatment of obesity.

One aspect the present invention is directed to a method for treating obesity in a subject in need thereof, comprising administering to the subject a therapeutically effective amount of a compound of Formula I:

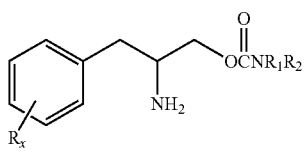

or a pharmaceutically acceptable salt or ester thereof; wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms; x is an integer of 0 to 3, with the proviso that R may be the same or different when x is 2 or 3; $R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom; wherein the subject reduces body weight, thereby treating the obesity.

In another aspect the present invention is directed to a method for reducing body weight or body weight gain in a subject in need thereof, comprising administering to the subject a therapeutically effective amount of a compound of Formula I:

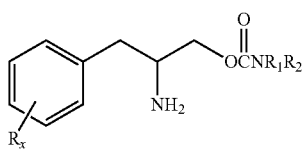

or a pharmaceutically acceptable salt or ester thereof; wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms; x is an integer of 0 to 3, with the proviso that R may be the same or different when x is 2 or 3; $R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom; wherein the subject reduces body weight.

In another aspect the present invention is directed to a method for reducing food intake in a subject in need thereof, comprising administering to the subject a therapeutically effective amount of a compound of Formula I:

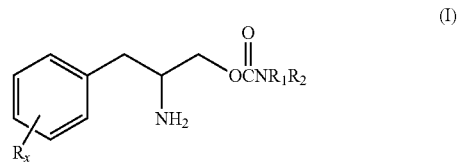

or a pharmaceutically acceptable salt or ester thereof; wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms; x is an integer of 0 to 3, with the proviso that R may be the same or different when x is 2 or 3; $R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom; wherein the subject reducing food intake.

In some embodiments, the subject is obese or morbidly obese and is in need of reducing weight or reducing/preventing further weight gain. In some embodiments, the subject is overweight and is in need of reducing body weight to the normal range and/or reducing/preventing further increase in body weight or becoming obese. In some embodiments, the subject is normal weight and wants to reducing/prevent an increase in body weight.

In some embodiments of the above methods, R is a member selected from the group consisting of alkyl of 1 to 3 carbon atoms, halogen, alkoxy of 1 to 3 carbon atoms, nitro, hydroxy, and trifluoromethyl. In some embodiments of the above methods, R is a member selected from the group consisting of alkyl of 1 to 3 carbon atoms, halogen, and alkoxy of 1 to 3 carbon atoms.

In some embodiments of the above methods, $R_1$ and $R_2$ are independently selected from the group consisting of hydrogen, alkyl of 1 to 8 carbon atoms, aryl, arylalkyl, and cycloalkyl of 3 to 7 carbon atoms. In some embodiments of the above methods, $R_1$ and $R_2$ are independently selected from the group consisting of hydrogen and alkyl of 1 to 8 carbon atoms. In some embodiments of the above methods, $R_1$ and $R_2$ are independently selected from the group consisting of hydrogen and alkyl of 1 to 3 carbon atoms.

It is understood that substituents and substitution patterns on the compounds of the present invention can be selected by one of skill in the art to provide compounds that are chemically stable and that can be readily synthesized by techniques known in the art as well as the methods provided herein.

In one embodiment, the compound of Formula I is a compound of Formula Ia:

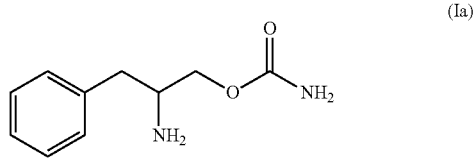 [SMILES: NC(=O)OCC(N)Cc1ccccc1]

(Ia)

or a pharmaceutically acceptable salt or ester thereof.

In one embodiment the compound of Formula I is the (D) enantiomer wherein $R_1$ and $R_2$ are hydrogen and x is 0 (compound Ib).

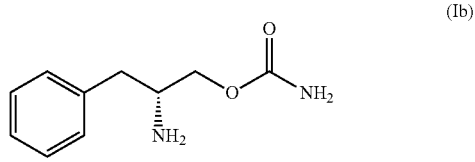 [SMILES: NC(=O)OC[C@H](N)Cc1ccccc1]

(Ib)

or a pharmaceutically acceptable salt or ester thereof. This compound is the (R) enantiomer, if named by structure and is therefore (R)-(beta-amino-benzenepropyl) carbamate. This compound is the dextrorotary enantiomer and can therefore also be named O-carbamoyl-(D)-phenylalaninol. These names may be used interchangeably in this specification.

The present invention includes the use of isolated enantiomers of the compound of Formula I (e.g., compounds of Formula Ia or Ib). In one embodiment, a pharmaceutical composition comprising the isolated S-enantiomer of Formula I is used to provide treatment to a subject. In another embodiment, a pharmaceutical composition comprising the isolated R-enantiomer of Formula I is used to provide treatment to a subject.

The present invention also includes the use of mixtures of enantiomers of Formula I. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one embodiment, the enantiomer that predominates in a composition comprising a compound of Formula I is the S-enantiomer of Formula I.

The present invention provides methods of using enantiomers and enantiomeric mixtures of compounds represented by Formula I. A carbamate enantiomer of Formula I contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer.

The term "substantially free," as used herein, means that the compound is made up of a significantly greater proportion of one enantiomer. In preferred embodiments, the compound includes at least about 90% by weight of one enantiomer. In other embodiments of the invention, the compound includes at least about 99% by weight of one enantiomer.

The compounds of Formula I can be synthesized by methods known to the skilled artisan. The salts and esters of the compounds of Formula I can be produced by treating the compound with a suitable mineral or organic acid (HX) in suitable solvent or by other means well known to those of skill in the art.

Details of reaction schemes for synthesizing compounds of Formula I as well as representative examples on the preparation of specific compounds have been described in U.S. Pat. No. 5,705,640, U.S. Pat. No. 5,756,817, U.S. Pat. No. 5,955,499, U.S. Pat. No. 6,140,532, all incorporated herein by reference in their entirety.

From Formula I it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art.

The compound may be administered to a subject by any conventional route of administration, including, but not limited to, oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intracerebralventricular, intrathecal, intracisternal, intraspinal or peri-spinal routes of administration by delivery via intracranial or intravertebral needles or catheters with or without pump devices. Depending on the route of administration, compounds of Formula I can be constituted into any form. For example, forms suitable for oral administration include solid forms, such as pills, gelcaps, tablets, caplets, capsules, granules, and powders (each including immediate release, timed release and sustained release formulations). Forms suitable for oral administration also include liquid forms, such as solutions, syrups, elixirs, emulsions, and suspensions. In addition, forms useful for parenteral administration include sterile solutions, emulsions and suspensions.

In certain embodiments, pharmaceutical compositions of this invention comprise one or more compounds of Formula I or a salt or ester thereof without any pharmaceutical carriers or excipients. In other embodiments, pharmaceutical compositions of this invention comprise one or more compounds of formula I or a salt or ester thereof intimately admixed with a pharmaceutical carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention, optionally in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin, or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93 (1997). The pharmaceutical formulations of the invention can also be in the form of oil-in-water emulsions. The oily phase can be a vegetable oil or a mineral oil, as described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using suitable dispersing or wetting agents and suspending agents. The sterile injectable preparation can also be a sterile injectable solution or suspension in a nontoxic parenterally acceptable diluent or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be administered orally. The amount of a compound of the present invention in the composition can vary widely depending on the type of composition, size of a unit dosage, kind of excipients, and other factors well known to those of skill in the art. In general, the final composition can comprise, for example, from 0.000001 percent by weight (% w) to 100% w of the carbamate compound, e.g., 0.00001% w to 50% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. In other embodiments, pharmaceutical formulations for oral administration can be formulated without using any pharmaceutically acceptable carriers.

Formulations suitable for oral administration can consist of (a) liquid solutions, such as an effective amount of the pharmaceutical formulation suspended in a diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen.

If desired, disintegrating or solubilizing agents can be added, such as cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187 (1995); Tjwa, Ann. Allergy Asthma Immunol. 75:107 (1995)).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater. Sci. Polym. Ed. 7:623 (1995); as biodegradable and injectable gel formulations (see, e.g., Gao, Pharm. Res. 12:857 (1995)); or, as microspheres for oral administration (see, e.g., Eyles, J. Pharm. Pharmacol. 49:669 (1997)). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. The active drug can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

By using liposomes, particularly where the liposome surface carries ligands specific for target cells, or are otherwise preferentially directed to a specific organ, one can focus the delivery of the carbamate compound into target cells in vivo (see, e.g., Al-Muhammed, J. Microencapsul. 13:293 (1996); Chonn, Curr. Opin. Biotechnol. 6:698 (1995); Ostro, Am. J. Hosp. Pharm. 46:1576 (1989)).

Active drug may also be delivered by the use of monoclonal antibodies as individual carriers to which the compound molecules are coupled. Active drug may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

In certain embodiments the compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 10 to about 1000 mg of the active ingredient, e.g., from about 25 to about 600 mg of the active ingredient, e.g., from about 75 to about 400 mg of the active ingredient, e.g., about 25, 50, 75, 100, 125, 150, 175, 200, 225, 250, 275, 300, 325, 350, 375, 400, 425, 450, 475, 500, 525, 550, 575, or 600 mg or more or any range therein.

In some embodiments of the present invention, carbamate compounds suitable for use in the practice of this invention will be administered either singly or concomitantly with at least one or more other compounds or therapeutic agents, e.g., with other agents that treat obesity and/or aid in reduction of body weight or food intake. Examples of therapeutic agents for treating obesity and reducing of body weight or food intake include, without limitation, leptin, leptin agonists, fenfluramine, dexfenfluramine, phentermine, sibutramine, orlistat, neuropeptide Y1 or Y5 antagonists, cannabinoid CB 1 receptor antagonists or inverse agonists (e.g., rimonabant (ACOMPLIA), otenabant, ibinabant, surinabant), melanocortin receptor agonists, in particular, melanocortin-4 receptor agonists, ghrelin antagonists, melanin-concentrating hormone (MCH) receptor antagonists, CD38 inhibitors, RP105 inhibitors, MD-1 inhibitors, PYY(3-36) or PYY(3-36) agonists, amylin or amylin agonists, a CCK or CCK agonists, exendin or exendin agonists, a CNTF or CNTF agonists, serotonin reuptake inhibitors, serotonin transport inhibitors, 5HT2c agonists, GLP-1 or GLP-1 agonists, DPP-IV inhibitors, opioid antagonists, orexin antagonists, metabotropic glutamate subtype 5 receptor antagonists, histamine 3 antagonist/inverse agonists, and topiramate.

In some embodiments, of the present invention, carbamate compounds suitable for use in the practice of this invention will be administered together with behavioral modifications, such as controlled diet and/or exercise.

The method includes the step of administering to a patient in need of treatment or prevention an effective amount of one of the carbamate compounds disclosed herein in combination with an effective amount of one or more other compounds or therapeutic agents that have the ability to provide advantageous combined effects such as the ability to augment the effects of the compounds of the invention.

Pharmaceutically acceptable salts and esters refers to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, trometh-amine, N methylglucamine, and the like. Pharmaceutically acceptable salts can also include acid addition salts formed from the reaction of amine moieties in the parent compound with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula I. More than one crystal form of an enantiomer of Formula I can exist and as such are also included in the present invention.

A pharmaceutical composition of the invention can optionally contain, in addition to a carbamate compound, at least one other therapeutic agent useful in the treatment of obesity and/or reduction in body weight and/or food intake. For example the carbamate compounds of Formula I can be combined physically with other compounds in fixed dose combinations to simplify their administration.

Methods of formulating pharmaceutical compositions have been described in numerous publications such as Pharmaceutical Dosage Forms: Tablets. Second Edition. Revised and Expanded. Volumes 1-3, edited by Lieberman et al.; Pharmaceutical Dosage Forms: Parenteral Medications. Volumes 1-2, edited by Avis et al.; and Pharmaceutical Dosage Forms: Disperse Systems. Volumes 1-2, edited by Lieberman et al.; published by Marcel Dekker, Inc, the disclosure of each of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

The present invention provides methods of providing treatment or prevention of obesity and/or reduction in body weight and/or food intake in a subject using carbamate compounds. The amount of the carbamate compound necessary to provide treatment or prevention of obesity is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of skill in the art will be able without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The Art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to provide treatment for cataplexy. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays).

Using such models, only ordinary calculations and adjustments are typically required to determine an appropriate concentration and dose to administer a therapeutically effective amount of the biologically active agent(s) (e.g., amounts that are orally effective intranasally effective, transdermally effective, intravenously effective, or intramuscularly effective to elicit a desired response). The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

Effective administration of the carbamate compounds of this invention can be, for example, at an oral or parenteral dose of from about 0.01 mg/kg/dose to about 150 mg/kg/dose. For example, administration can be from about 0.1/ mg/kg/dose to about 25 mg/kg/dose, e.g., from about 0.2 to about 18 mg/kg/dose, e.g., from about 0.5 to about 10 mg/kg/dose. Therefore, the therapeutically effective amount of the active ingredient can be, for example, from about 1 mg/day to about 7000 mg/day for a subject having, for example, an average weight of 70 kg, e.g., from about 10 to about 2000 mg/day, e.g., from about 50 to about 600 mg/day, e.g., about 10, 25, 50, 75, 100, 125, 150, 175, 200, 225, 250, 275, 300, 325, 350, 375, 400, 425, 450, 475, 500, 525, 550, 575, or 600 mg/day or more or any range therein. In one embodiment, the compound of Formula I is administered in the form of a capsule at a dose of about 150 mg to about 300 mg without any excipients.

The methods of this invention also provide for kits for use in providing treatment or prevention of obesity and/or reduction in body weight and/or food intake. After a pharmaceutical composition comprising one or more carbamate compounds of this invention, with the possible addition of one or more other compounds of therapeutic benefit, has been formulated in a suitable carrier, it can be placed in an appropriate container and labeled for providing treatment or prevention of obesity and/or reduction in body weight and/or food intake. Additionally, another pharmaceutical comprising at least one other therapeutic agent can be placed in the container as well and labeled for treatment of the indicated disease. Such labeling can include, for example, instructions concerning the amount, frequency and method of administration of each pharmaceutical.

Having described the present invention, the same will be explained in greater detail in the following examples, which are included herein for illustration purposes only, and which are not intended to be limiting to the invention.

EXAMPLE 1

Effect of R228060 on Body Weight and Food Consumption in Rats

A 6-month repeated dose oral toxicity study with 3-month recovery was carried out in rats for 8228060 (Formula Ib). Body weight and food consumption were monitored throughout the study.

Body Weight

Body weight and weight gain of males dosed with R228060 at 35 mg HCl-salt/kg body weight/day was slightly lower compared to control rats, reaching statistical significance from week 8 to week 12 (body weight gain: $p<0.05$) and from week 10 to 12 (body weight: $p<0.05$). Body weight gain was decreased with 6% in week 13 and with 5% in week 26. Oral dosing with R228060 at 35 mg HCl-salt/kg body weight/day for 6 consecutive months did not adversely affect body weight and body weight gain in female rats.

In males dosed at 300 mg HCl-salt/kg body weight/day, a pronounced decrease in body weight and body weight gain from the first week of dosing ($p<0.001$) was noted. Body weight gain was decreased with 27% in week 13 and with 24% in week 26. In females at the same dose level, body weight gain showed a moderate to pronounced decrease ($p<0.05$-$0.001$), especially towards the end of the dosing period. Body weight gain was 15% decreased compared to the control group in week 13, while a 23% decrease was noted in week 26. This resulted in a moderately decreased body weight ($p<0.05$-$0.001$).

Males dosed with R228060 at 600/450 mg HCl-salt/kg body weight/day showed a pronounced decrease in body weight and body weight gain from week 1 onwards ($p<0.001$). Body weight gain was decreased with 33% in week 13, and with 32% in week 26. In females, a moderate to pronounced decrease in body weight gain ($p<0.05$-$0.001$) was recorded from the first week of dosing. Body weight gain was decreased with 18% in week 13, and with 21% in week 26. This resulted in a moderately decreased body weight ($p<0.05$-$0.001$). As evidenced by the increase in body weight gain starting in the first week of recovery, male rats showed a partial regain of their normal (control) body weight after cessation of treatment. At the end of the three month recovery period the body weight was still moderately lower as compared to those of control animals. Similar findings were noted for females also resulting in a partial regain of their normal body weight. Compared to control animals the remaining body weight difference at the end of the recovery period was only slightly lower for the 600/450 mg HCl-salt/kg treated females.

In conclusion, body weights and body weight gains showed a dose-related decrease starting at 35 mg HCl-salt/kg body weight/day for males and 300 mg HCl-salt/kg body weight/day for females. At the end of the treatment period this resulted in decreases in body weight gain up to 32% and 21% for males and females respectively. After the 3-month recovery period the body weight losses were regained partially (males) to almost completely (females).

Food Consumption

Especially during the first weeks of dosing, for both sexes a dose-related decrease in food consumption was noted starting at 35 mg HCl-salt/kg body weight/day for males and 300 mg HCl-salt/kg body weight/day for females. This resulted in statistically significant decreases at the 300 and 600/450 mg HCl-salt/kg body weight level. Depending on the dose level, normal food consumption levels were regained in time. For males at the 600/450 mg HCl-salt/kg body weight level food intake recovered to normal approximately 12 weeks after initiation of treatment. For females this occurred earlier, food intake recovered to normal after about 4 weeks of treatment. In general, after regaining normal food consumption levels, no relevant changes in food intake were noted anymore. The noted statistically significant increases in food consumption at the 35, 300 and 600/450 mg HCl-salt/kg body weight level in females were considered to be toxicologically irrelevant.

In conclusion, dose-related decreases in food consumption were noted in both sexes especially in the first week(s) of dosing starting at 35 mg HCl-salt/kg body weight/day for males and 300 mg HCl-salt/kg body weight/day for females. At the 300 and 600/450 mg HCl-salt/kg body weight level, these decreases were statistically significant. Depending on the dose level and gender, normal food consumption levels were regained in time. Food consumption in males recovered later to normal levels as compared to females (respectively about 12 or 4 weeks after initiation of treatment).

EXAMPLE 2

Effect of 8228060 on Body Weight and Food Consumption in Dogs

A 52-week repeated dose oral toxicity study with 13-week recovery was carried out in beagle dogs for 8228060 (Formula Ib). Body weight and food consumption were monitored throughout the study (see Table 1).

Body Weight

Body weight losses were noted in all males treated at 25 or 50 mg/kg bw/day during the first 4 days of treatment, with a mean body weight loss of 0.3 kg and 0.7 kg, respectively. The mean body weight loss reached 0.8 kg on day 21 for the high dose male group and weights only returned to the initial values on day 126, while males receiving 25 mg/kg bw/day returned to initial weights on day 35.

Body weight loss was also noted in all treated females at 10, 25, or 50 mg/kg bw/day during the first 4 days of treatment, with a mean body weight loss of 0.4 kg, 0.5 kg and 0.7 kg, respectively. The mean body weight loss reached 0.8 kg on day 21 for the high dose female group and returned to the initial weight on day 77, while females receiving 10 or 25 mg/kg bw/day returned to the initial weight on day 28 and 42, respectively.

A lower does-relative mean body weight gain was generally noted on days 182 and 364 in treated groups, when compared to control.

Group 4 females had a higher body weight gain during the treatment-free period while gains were only slightly higher in group 4 males, when compared to controls.

TABLE 1

| Group | | Day 4 | Day 21 | Day 182 | Day 364 | Day 455 |
| --- | --- | --- | --- | --- | --- | --- |
| Control | males | −1% | +4% | +32% | +38% | +52% (+2%) |
|  | females | −1% | +1% | +33% | +47% | +65% (+1%) |
| 10 mg/kg bw/day | males | −1% | 0% | +22% | +32% | — |
|  | females | −6% | −2% | +26% | +25% | — |
| 25 mg/kg bw/day | males | −4% | −4% | +71% | +19% | — |
|  | females | −7% | −4% | +16% | +26% | — |
| 50 mg/kg bw/day | males | −9% | −12% | +7% | +9% | +12% (+6%) |
|  | females | −9% | −12% | +11% | +9% | +26% (+26%) |

Values indicated in brackets represent the variation during the treatment-free period only.

Food Consumption

One male receiving 25 mg/kg bw/day had reduced food consumption (about −40%) during the first week of treatment, when compared to control.

Males receiving 50 mg/kg bw/day had a reduced food consumption (about −50% of the daily portion) mainly during the first week of treatment, one being more affected and still having lower food consumption until day 42 as well as on several occasions at the end of the treatment period.

Three out of four females receiving 10 mg/kg bw/day had a slightly lower food consumption (about −25% of the daily portion) during the first week of treatment. Females receiving 25 mg/kg bw/day also had a lower food consumption (about −25 to −50% of the daily portion) during the first week of treatment. This was still noted on many occasions for two females throughout the treatment period. A lower food consumption, which was marked for 3/6 animals, was observed for all females receiving 50 mg/kg bw/day during the first week of treatment. Thereafter, food consumption generally returned to normal values with only sporadic changes during the rest of the treatment period. No effect on food consumption was noted for any animal during the treatment-free period.

EXAMPLE 3

Effect of 8228060 on Body Weight in Humans

A 6-week randomized, double blind, parallel group, active and placebo-controlled study was carried out to assess the efficacy of R228060 in adult subjects with major depressive disorder (MDD). Body weight was monitored throughout the study.

Table 2 summarizes the change in body weight from baseline to endpoint by treatment group. Subjects who received R228060 experienced a mean weight loss of 0.6 kg in the 200-mg group and 0.9 kg in the 400-mg group, while subjects who received placebo or paroxetine experienced mean weight gains of 0.7 and 0.1 kg, respectively.

TABLE 2

Body Weight - Change from Baseline to Endpoint

| Parameter:<br>Weight (kg) | Placebo<br>(N = 121) | R228060<br>200 mg<br>(N = 120) | R228060<br>400 mg<br>(N = 125) | Paroxetine<br>(N = 122) |
|---|---|---|---|---|
| Baseline | | | | |
| N | 117 | 116 | 120 | 117 |
| Mean (SD) | 85.4 (22.89) | 86.0 (23.90) | 84.1 (21.00) | 83.1 (21.77) |
| Median (Range) | 82.1 (48; 175) | 84.4 (46; 147) | 79.6 (44; 162) | 79.8 (42; 154) |
| End point | | | | |
| N | 117 | 116 | 120 | 117 |
| Mean (SD) | 86.1 (22.99) | 85.4 (24.03) | 83.2 (21.20) | 83.2 (22.06) |
| Median (Range) | 83.5 (48; 170) | 83.4 (46; 148) | 78.9 (44; 165) | 79.8 (42; 152) |
| Change from Baseline | | | | |
| N | 117 | 116 | 120 | 117 |
| Mean (SD) | 0.7 (1.78) | −0.6 (1.90) | −0.9 (2.20) | 0.1 (1.92) |
| Median (Range) | 0.6 (−5; 8) | −0.5 (−7; 5) | −0.9 (−9; 5) | 0.0 (−6; 7) |

SD = Standard deviation.

Table 3 shows the distribution of percent change in weight from baseline to endpoint by treatment group. Four subjects who received R228060 (1 [0.9%] in the 200-mg group, 3 [2.5%] in the 400-mg group) had a decrease in weight of 7% or more. The percentage of subjects whose weight was unchanged or decreased by less than 7% was greater in the R228060 groups than in the placebo or paroxetine groups. Correspondingly, the percentage of subjects who had a weight gain of <7% weight was higher in the placebo and paroxetine groups than in the R228060 groups.

TABLE 3

Body Weight - Distribution of Percent Change From Baseline to Endpoint

| Parameter<br>Character Value | Placebo<br>(N = 117)<br>n (%) | R228060<br>200 mg<br>(N = 116)<br>n (%) | R228060<br>400 mg<br>(N = 120)<br>n (%) | Paroxetine<br>(N = 117)<br>n (%) |
|---|---|---|---|---|
| Weight classification | 117 | 116 | 120 | 117 |
| Decrease ≥7% | 0 | 1 (0.9) | 3 (2.5) | 0 |
| No change/<br>decrease <7% | 40 (34.2) | 75 (64.7) | 90 (75.0) | 62 (53.0) |
| Increase <7% | 74 (63.2) | 39 (33.6) | 27 (22.5) | 54 (46.2) |
| Increase ≥7% | 3 (2.6) | 1 (0.9) | 0 | 1 (0.9) |

Mean changes from baseline to endpoint in BMI were small (−0.2 and −0.3 kg/m² for R228060 200 mg and 400 mg, respectively, versus 0.2 kg/m² and 0 for placebo and paroxetine, respectively).

All publications, patent applications, patents and other references cited herein are incorporated by reference in their entireties for the teachings relevant to the sentence and/or paragraph in which the reference is presented and for any other purpose for which it can be used.

We claim:

1. A method for treating pathological eating in a subject in need thereof, comprising administering to the subject a therapeutically effective amount of a compound of Formula (I):

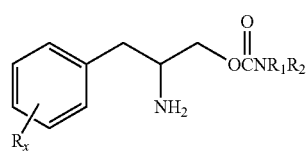

or a pharmaceutically acceptable salt or ester thereof;
wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms;
x is an integer of 0 to 3, with the proviso that R may be the same or different when x is 2 or 3;
$R_1$ and $R_2$ are independently selected from the group consisting of hydrogen, alkyl of 1 to 8 carbon atoms, aryl, arylalkyl, cycloalkyl of 3 to 7 carbon atoms; or
$R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom;
wherein the subject reduces body weight, thereby treating the obesity.

2. A method for preventing body weight gain in a subject in need thereof, comprising administering to the subject a therapeutically effective amount of a compound of Formula (I):

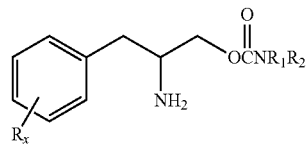

or a pharmaceutically acceptable salt or ester thereof;
wherein R is a member selected from the group consisting of alkyl of 1 to 8 carbon atoms, halogen, alkoxy of 1 to 3 carbon atoms, nitro, hydroxy, trifluoromethyl, and thioalkoxy of 1 to 3 carbon atoms;

x is an integer of 0 to 3, with the proviso that R may be the same or different when x is 2 or 3;

$R_1$ and $R_2$ are independently selected from the group consisting of hydrogen, alkyl of 1 to 8 carbon atoms, aryl, arylalkyl, cycloalkyl of 3 to 7 carbon atoms; or $R_1$ and $R_2$ can be joined to form a 5 to 7-membered heterocycle that is unsubstituted or substituted with one or more alkyl or aryl groups, wherein the heterocycle can comprise 1 to 2 nitrogen atoms and 0 to 1 oxygen atom, wherein the nitrogen atoms are not directly connected with each other or with the oxygen atom;

wherein the subject reduces body weight.

3. The method of claim 1, wherein x=0.

4. The method of claim 1, wherein $R_1$ and $R_2$ are hydrogen and x=0.

5. The method of claim 1, wherein the compound of Formula I is an enantiomer of Formula I substantially free of other enantiomers or an enantiomeric mixture wherein one enantiomer of Formula I predominates.

6. The method of claim 5, wherein the enantiomer of Formula I predominates to the extent of about 90% or greater.

7. The method of claim 5, wherein the enantiomer of Formula I predominates to the extent of about 98% or greater.

8. The method of claim 5, wherein the enantiomer of Formula I is an enantiomer of Formula Ia:

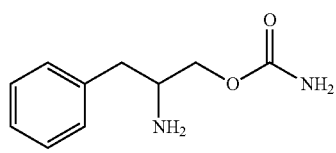

(Ia)

or a pharmaceutically acceptable salt or ester thereof.

9. The method of claim 8, wherein the enantiomer of Formula Ia is the (R) or (D) enantiomer.

10. The method of claim 8, wherein the enantiomer of Formula Ia is the (S) or (L) enantiomer.

11. The method of claim 8, wherein the enantiomer of Formula Ia predominates to the extent of about 90% or greater.

12. The method of claim 8, wherein the enantiomer of Formula Ia predominates to the extent of about 98% or greater.

13. The method of claim 5, wherein the enantiomer of Formula I substantially free of other enantiomers is the compound of Formula Ib or an enantiomeric mixture wherein the compound of Formula Ib predominates:

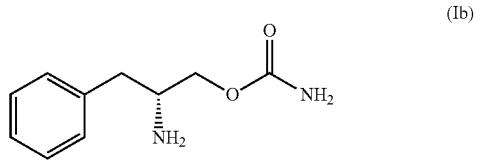 [SMILES: NC(=O)OC[C@H](N)Cc1ccccc1]

(Ib)

or a pharmaceutically acceptable salt or ester thereof.

14. The method of claim 13, wherein the compound of Formula Ib predominates to the extent of about 90% or greater.

15. The method of claim 13, wherein the compound of Formula Ib predominates to the extent of about 98% or greater.

16. The method of claim 1, wherein the effective amount of the compound of Formula I is from about 0.01 mg/kg/dose to about 150 mg/kg/dose.

17. The method of claim 1, wherein the effective amount of the compound of Formula I is from about 1 mg/day to about 7000 mg/day.

18. The method of claim 1, wherein the compound of Formula I is administered orally.

19. The method of claim 1, wherein the compound of Formula I is administered in the form of a capsule or tablet.

20. The method of claim 1, wherein the compound of Formula I is administered in the form of a capsule at a dose of about 10 mg to about 1000 mg without any excipients.

* * * * *